United States Patent
Spainhower

(10) Patent No.: US 8,752,554 B2
(45) Date of Patent: Jun. 17, 2014

(54) MOUTH GUARDS FOR TREATING OF TEMPOROMANDIBULAR DISORDER AND ASSOCIATED METHODS

(76) Inventor: David L. Spainhower, Layton, UT (US)

( * ) Notice: Subject to any disclaimer, the term of this patent is extended or adjusted under 35 U.S.C. 154(b) by 212 days.

(21) Appl. No.: 12/791,758

(22) Filed: Jun. 1, 2010

(65) Prior Publication Data

US 2011/0290261 A1 Dec. 1, 2011

(51) Int. Cl.
*A61C 5/14* (2006.01)
*A61F 5/56* (2006.01)

(52) U.S. Cl.
USPC .......................................... 128/859; 602/902

(58) Field of Classification Search
USPC ................... 128/859, 861, 862, 848; 433/6, 7; 602/902
See application file for complete search history.

(56) References Cited

U.S. PATENT DOCUMENTS

| | | | | |
|---|---|---|---|---|
| 2,855,670 A * | 10/1958 | Rose | ............................. | 433/215 |
| 3,207,153 A * | 9/1965 | Goldstein | ..................... | 128/862 |
| 3,478,429 A * | 11/1969 | Shilliday | .......................... | 433/6 |
| 4,370,129 A * | 1/1983 | Huge | ................................ | 433/6 |
| 4,773,853 A * | 9/1988 | Kussick | ........................... | 433/6 |
| 5,277,202 A * | 1/1994 | Hays | ............................. | 128/848 |
| 5,316,020 A * | 5/1994 | Truffer | ......................... | 128/848 |
| 5,829,441 A * | 11/1998 | Kidd et al. | .................... | 128/848 |
| 5,931,164 A * | 8/1999 | Kiely et al. | ................... | 128/859 |
| 5,947,918 A * | 9/1999 | Jones et al. | ..................... | 602/58 |
| 6,666,212 B2 * | 12/2003 | Boyd, Sr. | ...................... | 128/859 |
| 7,556,044 B2 * | 7/2009 | Ball | ............................... | 128/861 |
| 7,730,891 B2 * | 6/2010 | Lamberg | ....................... | 128/848 |
| 7,766,016 B2 * | 8/2010 | Orrico et al. | .................. | 128/848 |
| 8,105,210 B2 * | 1/2012 | Seybold | ......................... | 482/11 |
| RE43,459 E * | 6/2012 | Boyd, Sr. | ...................... | 128/859 |
| 2007/0023055 A1* | 2/2007 | Roth | ............................ | 128/861 |
| 2008/0138755 A1* | 6/2008 | Jansheski et al. | ................ | 433/6 |
| 2011/0240040 A1* | 10/2011 | Westbrook et al. | ........... | 128/860 |

* cited by examiner

*Primary Examiner* — Patricia Bianco
*Assistant Examiner* — Raymond E Harris
(74) *Attorney, Agent, or Firm* — Durham Jones & Pinegar Intellectual Property Law Group

(57) ABSTRACT

A mouth guard that may be used to treat temporomandibular disorder (TMD) is configured to eliminate pressure on an individual's back teeth. Such a mouth guard may also be configured to prevent a subject's lower jaw from moving in a posterior direction, or from "distalization." Methods for treating TMD include spacing the top teeth at the back of a subject's mouth from the bottom teeth at the back of the subject's mouth without applying pressure to either the top teeth or the bottom teeth.

20 Claims, 2 Drawing Sheets

MOUTH GUARDS FOR TREATING OF TEMPOROMANDIBULAR DISORDER AND ASSOCIATED METHODS

TECHNICAL FIELD

The present invention relates generally to mouth guards. More specifically, the present invention relates to mouth guards that may be used to treat temporomandibular disorder (TMD), and to methods for treating TMD. In particular, the present invention relates to mouth guards that are configured to eliminate pressure on an individual's back teeth.

BACKGROUND OF RELATED ART

Temporomandibular disorder (TMD), or temporomandibular joint disorder, is a broad term that refers to a variety of causes of and symptoms resulting from inflammation of the temporomandibular joint—the joint that connects the lower jaw, or mandible, to the skull. TMD may be caused by a number of factors, including, but not limited to, clenching or grinding of the teeth (during the day or night), trauma, repetitive unconscious jaw movements (or "bruxing"), a lack of symmetry in the relationship (e.g., spacing, etc.) between upper and lower teeth on each side of the head, and a variety of other factors.

There are a number of symptoms associated with TMD. Examples include, without limitation, jaw pain; pain in the temporomandibular joint or in the side of the face; clicking, popping or locking of the temporomandibular joint; sinus pain; ear pain; ringing in the ears, or "tinnitus;" a sense of fullness in the ears; tooth sensitivity; and tension headaches, among others. The symptoms of TMD may complicate daytime activities and interrupt restful sleep.

A number of devices, including a variety of mouth guards, have been developed in efforts to prevent TMD, but with limited effect.

SUMMARY

The present invention, in various aspects and embodiments, includes apparatus and methods for treating (e.g., reducing, eliminating, etc.) temporomandibular disorder, or TMD. As used herein, "temporomandibular disorder" and "TMD" include inflammation in tissues of the temporomandibular joint, as well as inflammation in tissues associated with the temporomandibular joint. In addition, the phrase "temporomandibular disorder" and its acronym "TMD," as used herein, also refer to symptoms of TMD, including, without limitation, jaw pain; pain in the temporomandibular joint or in the side of the face; clicking, popping or locking of the temporomandibular joint; sinus pain; ear pain; ringing in the ears, or "tinnitus;" a sense of fullness in the ears; tooth sensitivity; and tension headaches, as well as any other symptoms resulting from inflammation of tissues associated with the temporomandibular joint.

In one aspect, the present invention includes apparatus for treating TMD. In various embodiments, such an apparatus comprises a mouth guard. A mouth guard that incorporates teachings of the present invention may be configured to eliminate pressure on an individual's back teeth. Some embodiments of a mouth guard may also be configured to prevent a subject's lower jaw from moving in a posterior direction, or from distalization.

The present invention also includes methods for adapting an existing mouth guard design to prevent the existing mouth guard from applying pressure to an individual's back teeth.

According to another aspect, the present invention includes methods for treating TMD. A method of the present invention includes spacing upper teeth apart from lower teeth within a subject's mouth, while preventing pressure from being applied to teeth at or near the back of the subject's mouth. In some embodiments, a subject's upper and lower teeth are spaced apart while eliminating pressure on any of the subject's molars. Other embodiments of such a method additionally include avoiding the application of pressure to premolars in the subject's mouth.

TMD treatment methods may be effected during the daytime or at night. As such methods are often used at night, a mouth guard according to the present invention may also be referred to as a "night guard."

Other aspects and embodiments, as well as features and advantages of various aspects and embodiments, of the present invention will become apparent to those of ordinary skill in the art through consideration of the ensuing description, the accompanying drawings, and the appended claims.

DETAILED DESCRIPTION

Figure 5:
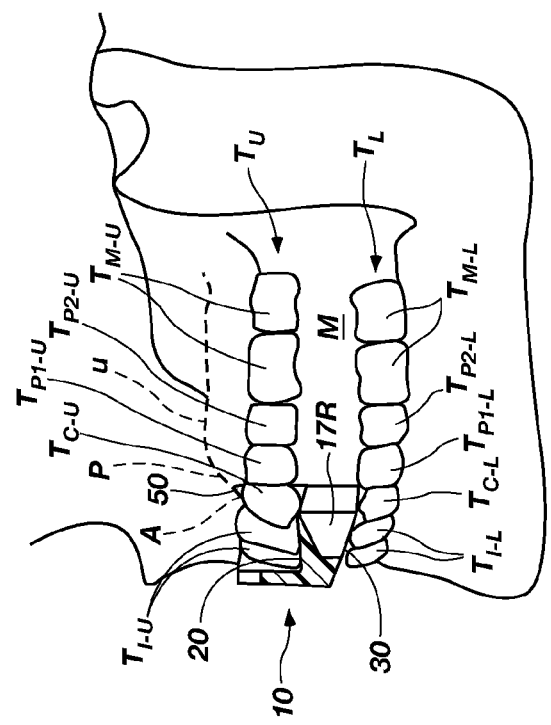
FIG. 5 is a sectional representation of the embodiment of mouth guard shown in FIGS. 1-4 within the mouth of a user.

The present invention, in various embodiments, includes mouth guards that may be used to treat temporomadibular disorder (TMD). One embodiment of such a mouth guard 10 is depicted in FIGS. 1-5, with FIGS. 1-4 illustrating features of the mouth guard 10 and FIG. 5 depicting placement of the mouth guard 10 within a subject's mouth M.

As depicted, a mouth guard 10 of the present invention may include an upper surface 20 and a lower surface 30. Both the upper surface 20 and the lower surface 30 may be curved to accommodate teeth T (including upper teeth $T_U$ and lower teeth $T_L$) within the mouth M of a subject. When the mouth guard 10 is in use within the mouth M of a subject, the upper teeth $T_U$ in the mouth M may rest against or engage the upper surface 20, while the lower teeth $T_L$ in the subject's mouth M may rest against or engage the lower surface 30.

In various embodiments, a mouth guard 10 of the present invention, and its upper and lower surfaces 20 and 30, may be configured to extend from a forward, or anterior, location in the mouth M of a subject to a location short of the most rearward, or posterior, locations within the subject's mouth M. In more specific embodiments, a mouth guard 10, or its outer edges E, may be configured to extend only to, or not substantially beyond, a subject's second premolars $T_{P2-L}$, $T_{P2-U}$. In other embodiments, the outer edges E of a mouth guard 10 of the present invention may extend only to, or not substantially beyond, a subject's first premolars $T_{P1-L}$, $T_{P1-U}$. Other embodiments of mouth guards 10 are configured to extend only to, or not substantially beyond, a subject's canines $T_{C-L}$, $T_{C-U}$.

While FIGS. 1-5 depict a mouth guard 10 that has been specifically designed to have a limited posterior extent, existing mouth guards may also be adapted to limit their posterior extents. Without limiting the scope of the present invention, the ends of an existing mouth guard may be trimmed away, reducing the posterior extent of the mouth guard. In some embodiments, an existing mouth guard may be trimmed so that as few as six (e.g., the incisors $T_{I-L}$, $T_{I-U}$ and canines $T_{C-L}$, $T_{C-U}$—FIG. 5) and as many as ten (the incisors $T_{I-L}$, $T_{I-U}$, canines $T_{C-L}$, $T_{C-U}$, first premolars $T_{P1-L}$, $T_{P1-U}$ and second premolars $T_{P2-L}$, $T_{P2-U}$—FIG. 5) top teeth and bottom teeth will be covered by or contact the mouth guard 10.

By limiting the posterior extent of the mouth guard 10, the mouth guard 10 spaces a subject's upper molars $T_{M-U}$ and, optionally, premolars $T_{P1-L}$, $T_{P1-U}$, $T_{P2-L}$, $T_{P2-U}$ apart from the subject's lower molars $T_{M-L}$ and, optionally, premolars $T_{P1-L}$, $T_{P1-U}$, $T_{P2-L}$, $T_{P2-U}$ without intervening material between these teeth. Without material between the upper molars $T_{M-U}$ and lower molars $T_{M-L}$ (and, optionally, the upper premolars $T_{P1-U}$, $T_{P2-U}$ and the lower premolars $T_{P1-L}$, $T_{P2-L}$), little or no pressure is applied to these teeth. As a result, the pressure or touching that may be sensed (i.e., proprioception) by the nerves associated with these teeth is reduced or eliminated. Contraction by muscles associated with the nerves, with the lower jaw, or mandible, and with the temporomandibular joint and, thus, clenching, may also be reduced or eliminated. In turn, inflammation of the temporomandibular joint (i.e., TMD), as well as the effects of such inflammation, and other problems associated with clenching may diminish or be eliminated.

From anterior locations to more posterior locations, the upper surface 20 of a mouth guard 10 of the present invention may slope or taper upward, while the lower surface 30 of the mouth guard 10 may slope or taper downward. In some embodiments, the slopes or tapers may begin at the most anterior edge 11 of the mouth guard 10 and continue to the most posterior edge 12 of the mouth guard 10. In other embodiments, the slopes or tapers may begin just posterior of (e.g., about 1 mm from, about 2 mm from, about 3 mm from, etc.) the most anterior edge 11 of the mouth guard 10.

One or both of the upper surface 20 and the lower surface 30 may be somewhat convex. In some embodiments, the most anterior locations 22 and 32 of the upper surface 20 and of the lower surface 30, respectively, may be substantially parallel to one another, while more posterior locations 24 and 34 of the upper surface 20 and the lower surface 30, respectively, may be spaced further apart at a center C of the mouth guard 10 than at outer edges E of the mouth guard 10.

The configuration (e.g., convexity, etc.) of the lower surface 30 may prevent the lower surface 30 from taking on a concave or upwardly sloped configuration as the shape of the lower surface 30 is tailored to an individual's bite (e.g., by way of the so-called "boil and bite" technique, etc.). Thus, the configuration of the lower surface 30 may prevent the lower surface 30 from assuming a configuration that may cause a subject's lower jaw, or mandible, to slide in a posterior direction, or to distalize, which may increase the stress on the temporomadibular joint.

Figure 7:
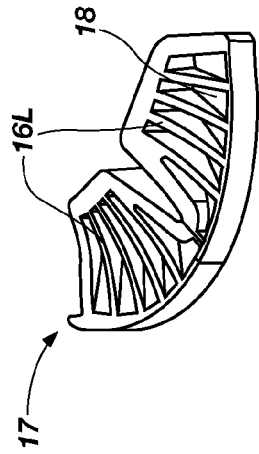
FIG. 7 is a perspective view of an upper section of the embodiment of mouth guard illustrated by FIG. 5.
Figure 8:
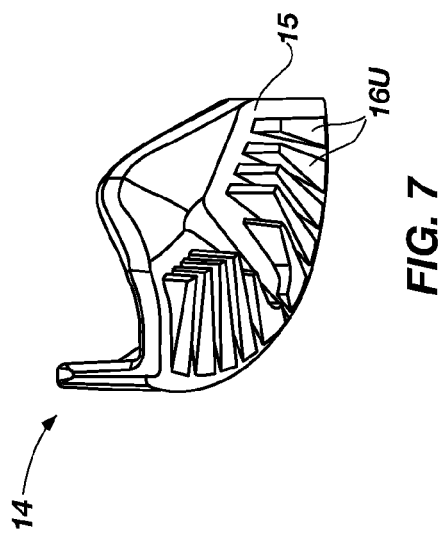
FIG. 8 is a perspective view of a lower section of the embodiment of mouth guard depicted by FIG. 5.
Figure 6:
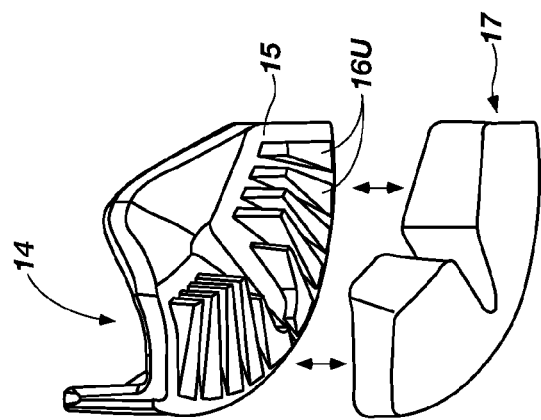
FIG. 6 is an assembly view of an embodiment of a mouth guard that includes at least two sections.

Some embodiments of mouth guards 10 that incorporate teachings of the present invention may include two or more sections that are secured to one another. These sections may be laminated to provide different surfaces or features of a mouth guard 10 with different characteristics. Such an embodiment is depicted by FIGS. 6-8. Specifically, the embodiment of mouth guard 10 shown in FIGS. 6-8 includes two laminated sections—an upper member 14 and a lower member 17. The upper and lower members 14 and 17 may be formed separately from one another, then secured to each other (e.g., separately formed members may be secured to one another with heat, adhesive, etc.; or one member (e.g., the lower member 17, etc.) may be formed (e.g., molded, etc.), then the other member (e.g., the upper member 14, etc.) formed (e.g., molded, etc.) on or against the previously formed member (e.g., the lower member 17, etc.) (e.g., by placing the previously formed member into a mold, then introducing liquefied material into the mold to form the other member, etc.); etc.).

The upper surface 20 of the mouth guard 10 is part of the upper member 14 of a two piece embodiment. Ribs 16U protrude from an opposite, inner surface 15 of the upper member 14. In the embodiment illustrated by FIGS. 6-8, the ribs 16U extend generally in an anterior-to-posterior direction, and are organized in a somewhat arcuate arrangement that substantially follows the curvature of the upper member 14 and, thus, of the mouth guard 10.

The lower surface 30 of the mouth guard 10 is defined by its lower member 17. The opposite, inner surface 18 of the lower member 17 also includes ribs 16L that protrude therefrom. As shown, ribs 16L may also comprise anteriorly-to-posteriorly extending elements that are organized in a generally arcuate arrangement. The ribs 16L of the lower member 17 may be positioned so as to cooperate (e.g., mesh, interleave, etc.) with the ribs 16U of the upper member 14 as the upper and lower members 14 and 17 are brought together in an assemble-assembled relationship.

When the upper and lower members 14 and 17 of the illustrated mouth guard 10 are properly formed or assembled with each other, the ribs 16U and 16L may be internally confined.

The ribs 16U and 16L may enable the shape of the mouth guard 10 to be customized in such a way as to optimize customization and/or performance of the mouth guard 10. As a non-limiting example, the ribs 16L of the lower member 17 may provide the lower member 17 with structure that counters the biting forces exerted by lower teeth (e.g., $T_{I-L}$, $T_{C-L}$, etc.). By counteracting the biting forces, the ribs 16L may reduce deformation of the lower surface 30. More specifically, the ribs 16L may reduce inversion of the lower surface 30 from convex or substantially flat to concave. A concave lower surface 30 could allow for distalization (i.e., posterior movement) of the lower jaw.

Figure 1:
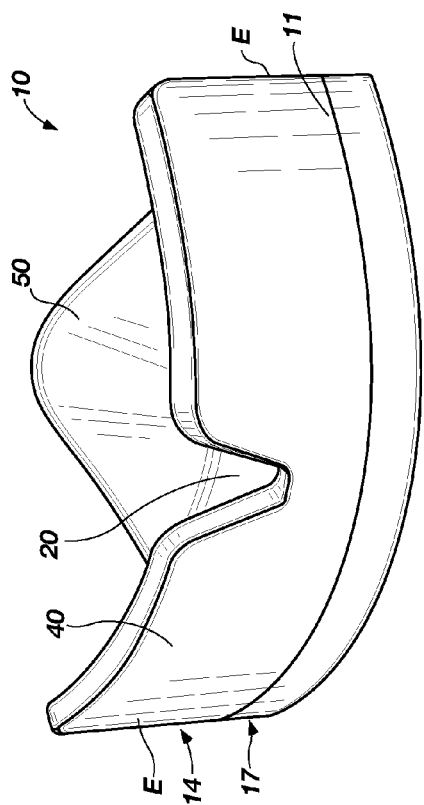
FIG. 1 is an upper rear perspective view of an embodiment of mouth guard that incorporates teachings of the present invention.
Figure 2:
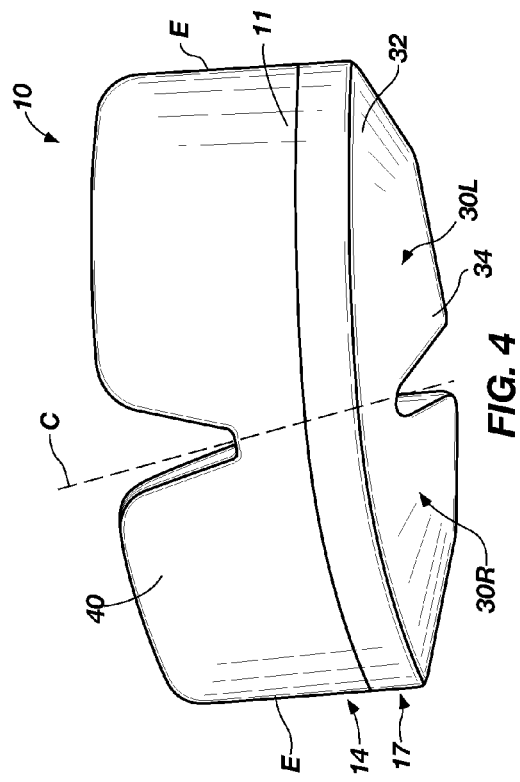
FIG. 2 is a lower rear perspective view of the embodiment of mouth guard shown in FIG. 1.
Figure 3:
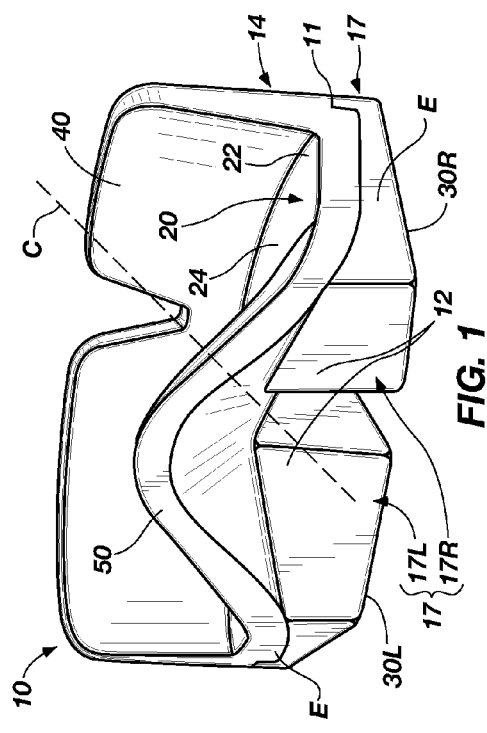
FIG. 3 is an upper front perspective view of the embodiment of mouth guard depicted by FIGS. 1 and 2.
Figure 4:
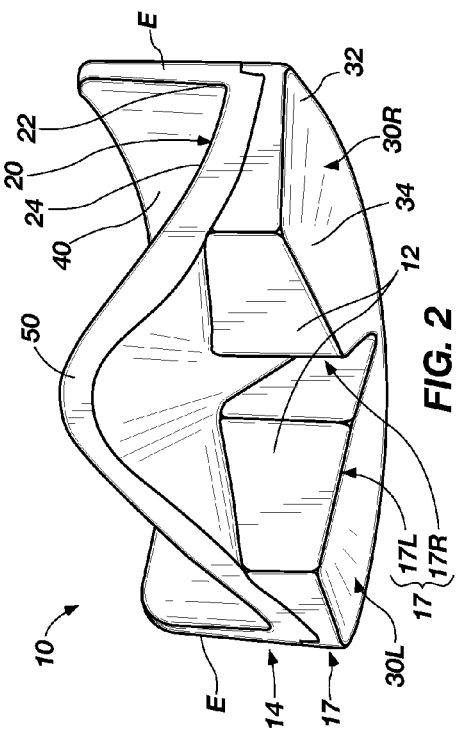
FIG. 4 is a lower front perspective view of the embodiment of mouth guard illustrated by FIGS. 1-3.

With returned reference to FIGS. 1 and 2, in some embodiments, one or more wedge-shaped gaps 19 (only one is depicted) may separate a lower portion (e.g., the lower member 17, etc.) of a mouth guard 10 of the present invention into two or more spaced apart sections 17L and 17R. Consequently, the lower surface 30 of such an embodiment of mouth guard 10 will also comprise two or more spaced apart sections 30L and 30R. In some embodiments, the wedge-shaped gap 19 and the spaced apart sections 17L and 17R may be configured to enable customization of the shape of the mouth guard 10 to a subject's mouth in a manner that optimizes performance of the mouth guard 10. As an example, the wedge-shaped gap 19 and spaced apart sections 17L and 17R may be configured to enable the lower surface 30 of the mouth guard 10 to conform to a wide variety of sizes and shapes of mouths M, while maintaining a convex or flat, but not concave, lower surface 30. Thus, in some embodiments, the wedge-shaped gap 19, the sections 17L and 17R spaced apart by the wedge-shaped gap 19, and the lower surface 30 may be configured to prevent distalization of the lower jaw. As another example, the wedge-shaped gap 19 may facilitate or even enable lateral customization of the mouth guard 10 (e.g., of the width of the mouth guard 10, etc.), including tailoring of the width of the mouth guard 10 to the width (e.g., narrow, wide, etc.) of a subject's mouth M.

Distalization of the lower jaw is known to stress the temporomandibular joint. The stress that results from distalization may cause the lower jaw to pinch so-called "retrodiscal" tissues in the temporomandibular joint. Pinching of the retrodiscal tissues may cause the muscles that move the lower jaw (and that control chewing, or mastication) to contract. Contraction of the muscles that move the lower jaw may trigger clenching of the jaws. Clenching is the root cause of TMD and a myriad of other problems. Features of a mouth guard 10 that prevent distalization may reduce or eliminate clenching, as well as other problems that result from clenching.

In addition to the upper and lower surfaces 20 and 30, as well as any or all of the other features described above, a mouth guard 10 that incorporates teachings of the present invention may include other elements. As shown in FIGS. 1-4, additional elements may include, but are certainly not limited to, features that are configured to retain the mouth guard 10 at a certain location and orientation within a subject's mouth.

One such feature is a rim 40 that protrudes upwardly from an anterior edge of the upper surface 20 of the mouth guard 10. The rim 40 is configured to be positioned between the upper teeth $T_U$ (e.g., the incisors $T_{I-L}$, $T_{I-U}$ and canines $T_{C-L}$, $T_{C-U}$, etc.) and the inner surface of the subject's mouth M (e.g., the top lip, etc.). The configuration of the rim 40, as well as its dimensions, may prevent mouth guard 10 from sliding further into the mouth M (i.e., in a posterior direction). In the depicted embodiment, the rim 40 will extend over much of the front surfaces of the upper teeth $T_U$, but stop just short of the gum line. Other rim configurations are also within the scope of the present invention, including short rims that protrude just enough to hold the mouth guard 10 in place, as well as longer rims that are configured to extend over attached and/or unattached gingiva.

A mouth guard 10 according to the present invention may include a palatal arch 50 to retain the mouth guard 10 at a desired location within a subject's mouth M. The palatal arch 50 may comprise a convex (when viewed from the front of the mouth guard 10) element that protrudes upwardly from a more posterior location of the upper surface 20 of the mouth guard 10. More specifically, the palatal arch 50 may be configured to extend up against an anterior surface A of the hard palate P within the subject's mouth M (see, e.g., FIG. 5). The configuration of the palatal arch 50 may prevent movement of the mouth guard 10 out of the subject's mouth M (i.e., movement in an anterior direction) when the mouth guard 10 has been properly positioned within the mouth M.

In some embodiments, the anterior-to-posterior extent of the palatal arch 50 may also be configured to minimize the potential for a gag reflex, or pharyngeal reflex, as the mouth guard 10 is placed within a subject's mouth M. In some embodiments, the palatal arch 50 is configured to be spaced well apart from the soft palate when the mouth guard 10 is placed within a subject's mouth M. The palatal arch 50 may also be configured to avoid encroachment of the space within the mouth M typically occupied by the tongue. For example, the palatal arch 50 may be configured to abut the anterior surface A of the hard palate P without extending a significant distance (e.g., more than about 5 mm, etc.) onto the upper surface U of the hard palate P. Alternatively, the palatal arch 50 may be configured to abut the anterior surface A of the hard palate P without extending onto the upper surface U of the hard palate P.

In other embodiments, a palatal arch may extend posteriorly beyond (e.g., more than 5 mm, etc.) the anterior surface A of the hard palate P. Such an embodiment may ensure better positioning and retention of the mouth guard 10 within the mouth M of a subject.

With both a rim 40 and a palatal arch 50, some embodiments of a mouth guard 10 of the present invention may be retained at a desired location within a subject's mouth M—at the front of the subject's mouth M, between the incisors $T_I$ and canines $T_C$, as seen in FIG. 5. When configured with appropriate dimensions, the rim 40 and palatal arch 50 may retain the mouth guard 10 within the mouth M of a subject with little or no risk of movement further into our out of the mouth M as the subject sleeps.

In a specific embodiment of a mouth guard 10 that incorporates teachings of the present invention, the most anterior locations of the upper surface 20 and the lower surface 30 may be spaced about 5 mm apart from one another. At the outer edges E of the mouth guard 10, the most posterior locations of the upper surface 20 and the lower surface 30 upon which teeth $T_U$ and $T_L$ may rest may be spaced about 2 mm or more (e.g., about 7 mm or about 8 mm, etc.) apart from one another, while at the center C of the mouth guard 10, the posterior locations of the upper surface 20 and the lower surface 30 may initially (in a pre-custom formed state) be spaced about 5 mm or more (e.g., about 15 mm, about 20 mm, etc.) apart from one another.

The rim 40 of such a mouth guard may protrude about 13 mm beyond the upper surface 20, while the palatal arch 50 may have a total height, measured at the posterior surfaces of the mouth guard 10, of about 20 mm. The top of such a mouth guard, along the center C from the anterior surface of the rim 40 to the posterior edge of the palatal arch 50, may measure about 23 mm. Of course, that dimension may vary with one or more of the thickness of the rim 40, the depth of the upper surface 20, and the posterior extent of the palatal arch 50. The bottom of such a mouth guard, along the center C from the anterior surface to the posterior surface, measures about 18 mm deep, but that dimension may be about 10 mm or less.

Of course, mouth guards with different configurations, including, without limitation, lateral (i.e., side-to-side) dimensions, anterior-to-posterior dimensions, heights, thicknesses, curvatures, angles, and other characteristics are also within the scope of the present invention.

As suggested previously herein, in some embodiments, a mouth guard 10 of the present invention, or at least the portions of the mouth guard 10 that define the upper surface 20 and the lower surface 30, may comprise a so-called "boil and bite material." A boil and bite material is a thermoplastic material that softens when heated (e.g., in hot or boiling water, etc.) and hardens when cooled. A nonlimiting example of such a material is ethylene-vinyl acetate (EVA).

In embodiments where a mouth guard 10 according to the present invention includes two or more sections, different sections may be formed from different materials. As an example, in the embodiment depicted by FIGS. 6-8, the material from which the upper member 14 is defined may be softer than the material that forms the lower member 17.

Use of a material of sufficient hardness at the bottom of the mouth guard 10 (e.g., to form the lower member 17, etc.) may prevent the lower surface 30 from becoming concave or from otherwise sloping from front to back as the shape of the mouth guard 10 is tailored (e.g., boiled and bitten) to conform to the features of a particular subject's mouth. Thus, the material from which the bottom of the mouth guard 10 is formed may prevent its lower surface 30 from taking on a configuration (e.g., a concave shape, etc.) that may allow or cause a subject's lower jaw, or mandible, to slide in a posterior direction, or distalize.

When a mouth guard 10 is formed from a thermoplastic boil and bite material, the mouth guard 10 may be fitted to a particular subject's, or individual's, mouth by heating the mouth guard 10 (e.g., in boiling water, etc.) to a sufficient temperature (e.g., 100° C., etc.) and for a sufficient period of time (e.g., about 30 seconds, etc.) to soften the same. Optionally, the mouth guard 10 may be allowed to cool somewhat (e.g., for about five or ten seconds, etc.) before being placed within the subject's mouth M. The mouth guard 10 is then placed within the subject's mouth M and molded to conform or substantially conform (e.g., to one or more, but not all, features within the subject's mouth, etc.) to the shape of the subject's mouth M as the mouth guard 10 cools. The subject may bite down on the mouth guard 10, but not through it. The subject may press (e.g., with fingers, lips, etc.) the front of the mouth guard 10 against the front surfaces of the gums and teeth between which it is disposed. The back portions of the mouth guard 10 may be shaped by pressing them (e.g., with the tongue, etc.) against corresponding surfaces (e.g., back surfaces of the teeth, the hard palate P, etc.) of the mouth M. As the subject molds the mouth guard 10, he or she may optimize conformation of the mouth guard 10 to the shape of the mouth M.

With the mouth guard 10 in place, as depicted by FIG. 5, upper teeth $T_U$ and lower teeth $T_L$ are spaced apart from each other, while little or no pressure is exerted against any back teeth (e.g., molars $T_{M-L}$, $T_{M-U}$, premolars $T_{P1-L}$, $T_{P1-U}$, $T_{P2-L}$, $T_{P2-U}$, etc.) within the subject's mouth M. The mouth guard 10 may be used while the subject is awake (e.g., during the daytime etc.) or as the subject sleeps (e.g., at night, etc.). When a mouth guard 10 conforms optimally to the shape of an individual subject's mouth M, the mouth guard 10 is more likely to remain within the subject's mouth M as the subject sleeps.

Also, as noted previously herein, one or more features (e.g., the shape of lower surface 30, ribs 16L, the wedge-shaped gap 19 and spaced apart sections 17L and 17R, etc.) of a mouth guard 10, when properly positioned within the mouth M of a subject, will prevent posterior movement, or distalization, of the subject's lower jaw, or mandible.

Although the foregoing description contains many specifics, these should not be construed as limiting the scope of the invention or of any of the appended claims, but merely as providing information pertinent to some specific embodiments that may fall within the scopes of the invention and the appended claims. Other embodiments of the invention may also be devised which lie within the scopes of the invention and the appended claims. Features from different embodiments may be employed in combination. The scope of the invention is, therefore, indicated and limited only by the appended claims and their legal equivalents. All additions, deletions and modifications to the invention, as disclosed herein, that fall within the meaning and scopes of the claims are to be embraced thereby.

What is claimed:

1. A mouth guard, comprising:
   a substrate configured to separate upper teeth within a mouth of a subject from lower teeth within the mouth of the subject without extending over any back teeth within the mouth of the subject, without applying pressure to any back teeth within the mouth of the subject as the subject bites down on the substrate and without covering buccal surfaces of the lower teeth; and
   a plurality of spaced apart support ribs internally confined within the substrate, each support rib of the plurality of spaced apart support ribs:
      being vertically oriented;
      having a length that extends in an anterior-to-posterior direction relative to at least one of anterior and posterior surfaces of the substrate and the mouth of the subject;
      including an anterior end positioned along an arc; and
      being configured to counter biting force exerted by the lower teeth to prevent a lower surface of the substrate from assuming a concave shape.

2. The mouth guard of claim 1, wherein the substrate includes an upper surface for engaging upper teeth within the mouth of the subject and a lower surface for engaging lower teeth within the mouth of the subject.

3. The mouth guard of claim 2, wherein the lower surface is convex, a shape of the lower surface being supported by the plurality of spaced apart support ribs.

4. The mouth guard of claim 3, wherein the lower surface includes at least two spaced apart sections.

5. The mouth guard of claim 4, wherein at least one gap between the at least two spaced apart sections enables conformation of the lower surface to a shape of the lower teeth in the mouth of the subject.

6. The mouth guard of claim 2, wherein the plurality of spaced apart support ribs is configured to prevent distalization of a lower jaw of the subject.

7. The mouth guard of claim 6, wherein the plurality of spaced apart support ribs is configured to: guide lower teeth within the mouth of the subject forward; or prevent the lower surface from becoming concave as the lower surface conforms to a shape of the lower teeth.

8. The mouth guard of claim 2, wherein the lower surface and the plurality of spaced apart support ribs comprise a harder material than the upper surface.

9. The mouth guard of claim 8, wherein the harder material of the lower surface prevents the lower surface from becoming concave as the lower surface conforms to a shape of the lower teeth.

10. The mouth guard of claim 2, comprising:
    an upper section defining the upper surface and comprising a first material; and
    a lower section defining the lower surface and comprising a second material.

11. The mouth guard of claim 10, wherein the second material is harder than the first material.

12. The mouth guard of claim 1, wherein the substrate is configured to separate the upper teeth from the lower teeth without applying pressure to any molars within the mouth of the subject.

13. The mouth guard of claim 12, wherein the substrate is further configured to separate the upper teeth from the lower teeth without applying pressure to any premolars within the mouth of the subject.

14. The mouth guard of claim 13, wherein the substrate is configured not to extend posteriorly beyond any canine teeth within the mouth of the subject.

15. The mouth guard of claim 12, wherein the substrate is configured not to extend posteriorly beyond any premolars within the mouth of the subject.

16. A method for treating temporomandibular joint disorder, comprising:

spacing upper teeth in a mouth of a subject from lower teeth in a mouth of a subject with a mouth guard without applying pressure to posterior teeth in the mouth of the subject; and preventing distalization of a mandible with a convex surface supported by a plurality of support ribs, each of which is within the mouth guard, vertically oriented and extends anteriorly-to-posteriorly relative to at least one of anterior and posterior surfaces of the mouth guard and the mouth of the subject, the plurality of support ribs being configured to prevent the convex surface from assuming a concave shape.

17. The method of claim 16, wherein spacing includes placing an element between upper front teeth and lower front teeth in the mouth of the subject while leaving free space between upper and lower posterior teeth.

18. The method of claim 17, wherein leaving free space between upper and lower posterior teeth includes leaving free space between upper and lower molars.

19. The method of claim 16, further comprising:
countering biting forces exerted by the lower teeth with the plurality of support ribs.

20. A mouth guard, comprising:
a substrate, including:
an upper element formed from a first material conformable to a shape of upper front teeth in a mouth of a subject, the upper element including:
a substantially arcuate, convex upper surface for receiving the upper front teeth, the upper surface having a posterior extent configured to terminate short of a location of molars in the mouth of the subject;
a rim protruding from an anterior edge of the upper surface;
a palatal arch protruding from a posterior edge of the upper surface; and
an inner surface; and
a lower element for receiving cutting surfaces of the lower front teeth without covering buccal surfaces of the lower front teeth, the lower element formed from a second material, the second material being harder than the first material, the lower element including:
an inner surface configured for placement against the inner surface of the upper element; and
a substantially arcuate, convex lower surface against which the lower front teeth may rest, the second material being configured to maintain a convexity of the convex lower surface when the convex lower surface is subjected to biting force exerted by the lower front teeth, the lower surface having a posterior extent configured to terminate short of a location of molars in the mouth of the subject, the lower surface including two side sections spaced apart from one another by a central gap; and a plurality of support ribs associated with the inner surface of the lower element, each rib of the plurality of support ribs extending in an anterior-to-posterior direction, the plurality of support ribs being configured to prevent the lower surface of the lower element from assuming a concave shape.

* * * * *

UNITED STATES PATENT AND TRADEMARK OFFICE
CERTIFICATE OF CORRECTION

PATENT NO. : 8,752,554 B2
APPLICATION NO. : 12/791758
DATED : June 17, 2014
INVENTOR(S) : David L. Spainhower It is certified that error appears in the above-identified patent and that said Letters Patent is hereby corrected as shown below:

In the Specification

Column 4, Line 32, delete "assemble-"

Signed and Sealed this
Seventh Day of October, 2014

Michelle K. Lee
*Deputy Director of the United States Patent and Trademark Office*